United States Patent
Lidgren et al.

(10) Patent No.: US 7,935,121 B2
(45) Date of Patent: May 3, 2011

(54) DEVICE FOR PROVIDING SPONGY BONE WITH BONE SUBSTITUTE AND/OR BONE REINFORCING MATERIAL, BONE SUBSTITUTE AND/OR BONE REINFORCING MATERIAL AND METHOD

(75) Inventors: Lars Lidgren, Lund (SE); Torgny Lundgren, Eslöv (SE); Pär Arvidsson, Lund (SE); Sven Jönsson, Staffanstorp (SE)

(73) Assignee: Bone Support AB, Lund (SE)

( * ) Notice: Subject to any disclaimer, the term of this patent is extended or adjusted under 35 U.S.C. 154(b) by 1025 days.

(21) Appl. No.: 10/578,734

(22) PCT Filed: Nov. 10, 2004

(86) PCT No.: PCT/SE2004/001626
§ 371 (c)(1),
(2), (4) Date: May 10, 2006

(87) PCT Pub. No.: WO2005/044154
PCT Pub. Date: May 19, 2005

(65) Prior Publication Data
US 2007/0161943 A1    Jul. 12, 2007

(30) Foreign Application Priority Data
Nov. 11, 2003   (SE) ...................................... 0302983

(51) Int. Cl.
*A61M 37/00*    (2006.01)
(52) U.S. Cl. ................. 606/92; 606/93; 604/19
(58) Field of Classification Search ............ 606/92, 606/93, 79, 86 R, 80, 94; 604/19, 27; 366/139
See application file for complete search history.

(56) References Cited

U.S. PATENT DOCUMENTS

| 949,163 A | 2/1910 | Stapley |
|---|---|---|
| 1,644,173 A | 10/1927 | Carr |
| 3,367,783 A | 2/1968 | Billerbeck |

(Continued)

FOREIGN PATENT DOCUMENTS

DE            44 09 610 A1     9/1995

(Continued)

OTHER PUBLICATIONS

Aebli et al., "Cardiovascular Changes During Multiple Vertebroplasty With and Without Vent-Hole: An Experimental Study in Sheep", Spine 2003; 28(14)1504-11.

(Continued)

*Primary Examiner* — Eduardo C Robert
*Assistant Examiner* — Jan Christopher Merene
(74) *Attorney, Agent, or Firm* — Finnegan, Henderson, Farabow, Garrett & Dunner

(57) ABSTRACT

The present invention relates to a device for providing spongy bone with bone substitute and/or bone reinforcing material, wherein at least one perforating device (4) is provided for making at least one hole (5) in the spongy bone (1) and wherein at least one flushing or rinsing device (6) is provided for flushing or rinsing the hole (5) with a rinsing agent (7). At least one vacuum source (9) is provided for generating a vacuum in the hole (5) in the spongy bone (1) for sucking and/or facilitating insertion or feeding of the bone substitute and/or bone reinforcing material (3) into said spongy bone (1). The invention also relates to bone substitute and/or bone reinforcing material and methods in connection with the invention.

56 Claims, 4 Drawing Sheets

U.S. PATENT DOCUMENTS

| | | | |
|---|---|---|---|
| 3,475,010 A | | 10/1969 | Cook et al. |
| 3,837,379 A | * | 9/1974 | McDonald et al. ............ 141/232 |
| 3,965,910 A | * | 6/1976 | Fischer ........................ 604/249 |
| 4,001,323 A | | 1/1977 | Felder et al. |
| 4,139,605 A | | 2/1979 | Felder et al. |
| 4,269,331 A | | 5/1981 | Watson |
| 4,338,925 A | | 7/1982 | Miller |
| 4,348,377 A | | 9/1982 | Felder et al. |
| 4,487,766 A | | 12/1984 | Mach |
| 4,496,342 A | * | 1/1985 | Banko .............................. 604/27 |
| 4,583,974 A | | 4/1986 | Kokernak |
| 4,619,655 A | | 10/1986 | Hanker et al. |
| 4,676,655 A | | 6/1987 | Handler |
| 4,721,390 A | * | 1/1988 | Lidgren ........................ 366/139 |
| 4,752,479 A | | 6/1988 | Briggs et al. |
| 4,994,442 A | | 2/1991 | Gil et al. |
| 5,047,030 A | * | 9/1991 | Draenert ........................ 606/65 |
| 5,071,040 A | | 12/1991 | Laptewicz, Jr. |
| 5,073,362 A | | 12/1991 | Blaszkiewicz et al. |
| 5,149,368 A | | 9/1992 | Liu et al. |
| 5,168,757 A | | 12/1992 | Rabenau et al. |
| 5,232,024 A | | 8/1993 | Williams |
| 5,262,166 A | | 11/1993 | Liu et al. |
| 5,269,785 A | * | 12/1993 | Bonutti ............................ 606/80 |
| 5,281,265 A | | 1/1994 | Liu |
| 5,328,262 A | | 7/1994 | Lidgren et al. |
| 5,342,441 A | | 8/1994 | Manadel et al. |
| 5,360,823 A | | 11/1994 | Griffel et al. |
| 5,403,318 A | * | 4/1995 | Boehringer et al. ............ 606/82 |
| 5,447,711 A | | 9/1995 | Almen et al. |
| 5,462,722 A | | 10/1995 | Liu et al. |
| 5,501,520 A | | 3/1996 | Lidgren et al. |
| 5,549,380 A | | 8/1996 | Lidgren et al. |
| 5,551,778 A | | 9/1996 | Hauke et al. |
| 5,605,885 A | | 2/1997 | Bernton et al. |
| 5,614,206 A | | 3/1997 | Randolph et al. |
| 5,650,108 A | | 7/1997 | Nies et al. |
| 5,681,873 A | | 10/1997 | Norton et al. |
| 5,695,742 A | | 12/1997 | Felder et al. |
| 5,698,186 A | | 12/1997 | Weeks |
| 5,797,873 A | | 8/1998 | Franz et al. |
| 5,829,875 A | | 11/1998 | Hagel et al. |
| 5,837,752 A | | 11/1998 | Shastri et al. |
| 5,842,786 A | | 12/1998 | Solomon |
| 5,866,100 A | | 2/1999 | Tournier et al. |
| 5,871,549 A | | 2/1999 | Jayashankar et al. |
| 5,891,423 A | | 4/1999 | Weeks |
| 5,965,772 A | | 10/1999 | Desantis |
| 5,997,544 A | * | 12/1999 | Nies et al. ........................ 606/92 |
| 6,018,094 A | | 1/2000 | Fox |
| 6,018,095 A | | 1/2000 | Lerch et al. |
| 6,071,982 A | | 6/2000 | Wise et al. |
| 6,074,358 A | * | 6/2000 | Andrew et al. ................. 604/28 |
| 6,075,067 A | | 6/2000 | Lidgren |
| 6,080,801 A | | 6/2000 | Draenert et al. |
| 6,118,043 A | | 9/2000 | Nies et al. |
| 6,120,174 A | | 9/2000 | Hoag et al. |
| 6,206,957 B1 | | 3/2001 | Driessens et al. |
| 6,231,615 B1 | | 5/2001 | Preissman |
| 6,248,110 B1 | | 6/2001 | Reiley et al. |
| 6,251,139 B1 | | 6/2001 | Lin et al. |
| 6,309,420 B1 | | 10/2001 | Preissman |
| 6,365,218 B1 | | 4/2002 | Borschel et al. |
| 6,431,743 B1 | | 8/2002 | Mizutani et al. |
| 6,440,138 B1 | | 8/2002 | Reiley et al. |
| 6,447,809 B1 | | 9/2002 | Krumhar et al. |
| 6,488,651 B1 | | 12/2002 | Morris et al. |
| 6,586,009 B1 | | 7/2003 | Lidgren |
| 6,596,904 B1 | | 7/2003 | Dunn et al. |
| 6,689,375 B1 | | 2/2004 | Wahlig et al. |
| 6,706,069 B2 | | 3/2004 | Berger |
| 6,706,273 B1 | | 3/2004 | Roessler |
| 6,716,216 B1 | | 4/2004 | Boucher et al. |
| 6,719,761 B1 | | 4/2004 | Reiley et al. |
| 6,723,334 B1 | | 4/2004 | McGee et al. |
| 6,736,537 B2 | | 5/2004 | Coffeen et al. |
| 6,740,090 B1 | | 5/2004 | Cragg et al. |
| 6,897,339 B2 | | 5/2005 | Turchetta et al. |
| 7,160,306 B2 | | 1/2007 | Matsuzaki et al. |
| 7,393,342 B2 | | 7/2008 | Henniges et al. |
| 7,417,077 B2 | | 8/2008 | Lidgren et al. |
| 7,524,103 B2 | | 4/2009 | McGill et al. |
| 2001/0012968 A1 | | 8/2001 | Preissman |
| 2001/0051670 A1 | | 12/2001 | Goupil et al. |
| 2002/0055143 A1 | | 5/2002 | Bell et al. |
| 2002/0076378 A1 | | 6/2002 | Wolfe et al. |
| 2002/0156483 A1 | * | 10/2002 | Voellmicke et al. ............ 606/93 |
| 2002/0169506 A1 | | 11/2002 | Matsushima et al. |
| 2003/0028251 A1 | | 2/2003 | Mathews |
| 2003/0050702 A1 | | 3/2003 | Berger |
| 2003/0055512 A1 | | 3/2003 | Genin et al. |
| 2003/0109883 A1 | | 6/2003 | Matsuzaki et al. |
| 2003/0161858 A1 | | 8/2003 | Lidgren |
| 2004/0006347 A1 | | 1/2004 | Sproul |
| 2004/0049202 A1 | | 3/2004 | Berger |
| 2004/0151751 A1 | | 8/2004 | Cooper |
| 2004/0191897 A1 | * | 9/2004 | Muschler ....................... 435/325 |
| 2004/0244651 A1 | | 12/2004 | Lemaitre et al. |
| 2005/0023171 A1 | | 2/2005 | Delaney et al. |
| 2005/0105385 A1 | | 5/2005 | McGill et al. |
| 2005/0119746 A1 | | 6/2005 | Lidgren |
| 2005/0128868 A1 | | 6/2005 | Vries |
| 2005/0241535 A1 | | 11/2005 | Bohner |
| 2005/0251149 A1 | | 11/2005 | Wenz |
| 2005/0257714 A1 | | 11/2005 | Constanz et al. |
| 2005/0287071 A1 | | 12/2005 | Wenz |
| 2006/0004358 A1 | | 1/2006 | Serhan et al. |
| 2006/0036211 A1 | | 2/2006 | Solsberg et al. |
| 2006/0041033 A1 | | 2/2006 | Bisig et al. |
| 2006/0122621 A1 | * | 6/2006 | Truckai et al. .................. 606/93 |
| 2007/0041906 A1 | | 2/2007 | Lidgren et al. |
| 2007/0161943 A1 | | 7/2007 | Lidgren et al. |
| 2007/0217282 A1 | | 9/2007 | Lidgren et al. |
| 2008/0318862 A1 | | 12/2008 | Ashman et al. |
| 2010/0008181 A1 | | 1/2010 | Lidgren et al. |

FOREIGN PATENT DOCUMENTS

| | | |
|---|---|---|
| EP | 0 023 992 A1 | 2/1981 |
| EP | 0 109 310 B1 | 5/1984 |
| EP | 0 308 364 A2 | 3/1989 |
| EP | 0 495 284 A1 | 7/1992 |
| EP | 0 639 382 A1 | 2/1995 |
| EP | 0 639 382 B1 | 2/1995 |
| EP | 0 657 208 A1 | 6/1995 |
| EP | 0 520 690 B1 | 11/1995 |
| EP | 0 807 432 B1 | 11/1997 |
| EP | 0 950 420 A2 | 10/1999 |
| EP | 1 155 704 A1 | 11/2001 |
| EP | 1 208 850 A1 | 5/2002 |
| EP | 1 132 061 B1 | 8/2004 |
| ES | 1 155 704 | 11/2001 |
| ES | 2 178 556 | 12/2002 |
| GB | 2 239 818 A | 7/1991 |
| JP | 64-22256 A | 1/1989 |
| JP | 64-22257 A | 1/1989 |
| JP | 1-139516 | 6/1989 |
| JP | 5-168692 A | 7/1993 |
| JP | 5-507862 A | 11/1993 |
| JP | 6-84289 | 6/1994 |
| JP | 2935708 B2 | 6/1999 |
| JP | 2000-295 A | 1/2000 |
| JP | 2001-106638 A | 4/2001 |
| JP | 2001-510078 A | 7/2001 |
| JP | 2001-517997 A | 10/2001 |
| JP | 2001-517997 T | 10/2001 |
| JP | 2002-058736 A | 2/2002 |
| JP | 2002-325831 A | 11/2002 |
| JP | 2003-507090 A | 2/2003 |
| SE | 8903538 | 4/1991 |
| WO | WO 85/01727 A1 | 4/1985 |
| WO | WO 87/05521 A1 | 9/1987 |
| WO | WO 88/06023 | 8/1988 |
| WO | WO 89/03695 A1 | 5/1989 |
| WO | WO 91/00252 A1 | 1/1991 |
| WO | WO 91/17722 A1 | 11/1991 |
| WO | WO 96/39202 A1 | 12/1996 |
| WO | WO 97/38676 A1 | 10/1997 |

| | | | |
|---|---|---|---|
| WO | WO 97/47334 A1 | 12/1997 |
| WO | WO 99/17710 A1 | 4/1999 |
| WO | WO 99/62570 A1 | 12/1999 |
| WO | WO 99/65597 A1 | 12/1999 |
| WO | WO 00/02597 A1 | 1/2000 |
| WO | WO 00/45867 A1 | 8/2000 |
| WO | WO 01/34216 A1 | 5/2001 |
| WO | WO 02/05861 A1 | 1/2002 |
| WO | WO 02/058755 A2 | 8/2002 |
| WO | WO 02/080933 A1 | 10/2002 |
| WO | WO 03/037165 A2 | 5/2003 |
| WO | WO 03/041753 A1 | 5/2003 |
| WO | WO 03/053488 A1 | 7/2003 |
| WO | WO 2004/000374 A1 | 12/2003 |
| WO | WO 04/002615 A1 | 1/2004 |
| WO | WO 2004/026377 A1 | 4/2004 |
| WO | WO 2006/041365 A1 | 4/2006 |

OTHER PUBLICATIONS

Koessler et al., "Fat and Bone Marrow Embolism During Percutaneous Vertebroplasty", Anesth Analg 2003; 97:293-294.

Lidgren., "Bone Substitutes", Karger Gazette No. 65 2003; Bone and Joints.

Kirby et al., "Acute Bronchospasm Due to Exposure to Polymethacrylate Vapours During Percutaneous Vertebroplasty", AJR J Roentgenol. Feb. 2003; 180(2):543-4.

English language abstract of JP 5-168692 A.

English language abstract of JP 2000-295 A.

English language abstract of JP 2001-106638 A.

English language abstract of JP 5-507862 A.

English language translation of Jun. 2, 2009, Office Action in Japanese Application No. 2003-554244.

English language translation of JP 64-22256.

English language translation of JP 64-22257.

Office Action in copending U.S. Appl. No. 10/547,671 dated Aug. 5, 2009.

Office Action in copending U.S. Appl. No. 12/122,873 dated Jun. 19, 2009.

Office Action in copending U.S. Appl. No. 12/219,542 dated Jun. 19, 2009.

Barbalace, K. "Chemical Database: Calcium sulfate", Environmental Chemistry.com, 2009, 3 pages.

Bohner, M., "Physical and chemical aspects of calcium phosphates used in spinal surgery", Eur. Spine J. (2001) 10:S114-S121.

Copending U.S. Appl. No. 12/122,873, filed May 19, 2008.

Copending U.S. Appl. No. 12/219,542, filed Jul. 23, 2008.

Copending U.S. Appl. No. 12/219,543, filed Jul. 23, 2008.

Eromosele et al., "Characterization and viscosity parameters of seed oils from wild plants", Science Direct: Bioresource Technology, 2002, 7 pages.

Nilsson et al., "The Effect of Aging an Injectable Bone Graft Substitute in Simulated Body Fluid," Key Engineering Materials, vols. 240-242 (2003), pp. 403-406.

"Powder (substance)" entry from www.wikipedia.com, <<http://en.wikipedia.org/wiki/Powder_(substance)>> (last visited Dec. 1, 2008)(4 pgs.).

Bohner et al., "Effects of Sulfate Ions on the In Vitro Properties of β-TCP-MCPM-Water Mixtures. Preliminary In Vivo Results,"Bioceramics: Materials and Applications, Ceramic Transactions, vol. 48 (1995), pp. 245-259.

Bohner, "New hydraulic cements based on α-tricalcium phosphate-calcium sulfate dihydrate mixtures," Biomaterials (2004) 25, 741-749.

Cabanas, "Setting Behavior and in Vitro Bioactivity of Hydroxyapatite/Calcium Sulfate Cements," Chem. Mater. (2002) 14, 3550-3555.

Database Derwent WPI: Week 198928, Derwent Publications Ltd., JP 1139516.

Database Derwent WPI: Week 199126, Derwent Publications Ltd., SE 8903538.

Database Derwent WPI: Week 199433, Derwent Publications Ltd., London, GB: Class A 96, AN 1994-269325 & JP 61-99623 A (Lion Corp. et al.), Jul. 19, 1994.

Database Derwent WPI: Week 200138, Derwent Publications Ltd., WO 2001/34216 A1.

Database Derwent WPI: Week 199734, Derwent Publications Ltd., EP 0807432 B1.

English-Language Abstract of EP 0 657 208 A1.

English-Language translation of JP 1-139516.

English-language translation of SE 8903538, "Implant material and method for the manufacture thereof," Bioapatite AB.

Engqvist et al., "Chemical Stability of a Novel Injectable Bioceramic for Stabilisation of Vertebral Compression Fractures," Trends Biomater. Artif. Organs (2008) 21(2):98-106.

Ima-Nirwana et al., "Palm vitamin E improves bone metabolism and survival rate in thyrotoxic rats," Gen. Pharmacol. (1999) 32:621-626.

International Preliminary Examination Report for PCT/SE01/00789 dated Jan. 11, 2002, related to U.S. Appl. No. 10/257,561.

International Preliminary Examination Report for PCT/SE01/01627 dated Oct. 14, 2002, related to U.S. Appl. No. 10/333,026.

International Preliminary Examination Report for PCT/SE02/02428 dated Mar. 16, 2004, related to U.S. Appl. No. 10/499,023.

International Preliminary Examination Report for PCT/SE2004/000328 dated Aug. 30, 2005, related to U.S. Appl. No. 10/547,671.

International Preliminary Report on Patentability for PCT/SE2004/001626 dated Feb. 13, 2006.

International Preliminary Report on Patentability for PCT/SE2005/000932 dated Dec. 28, 2006.

International Search Report for PCT/SE01/00789 dated Jul. 9, 2001, related to U.S. Appl. No. 10/257,561.

International Search Report for PCT/SE01/01627 dated Dec. 18, 2001, related to U.S. Appl. No. 10/333,026.

International Search Report for PCT/SE02/02428 dated Apr. 4, 2003, related to U.S. Appl. No. 10/499,023.

International Search Report for PCT/SE2004/000328 dated Jun. 8, 2004, related to U.S. Appl. No. 10/547,671.

International Search Report for PCT/SE2004/001626 dated Feb. 28, 2005.

Mirtchi et al., "Calcium phosphate cements: action of setting regulators on the properties of the β-tricalcium phosphate-monocalcium phosphate cements," Biomaterials (1989), 10(9), pp. 634-638.

International Search Report for PCT/SE2005/000932 dated Oct. 10, 2005.

Komath et al., "On the development of an apatic calcium phosphate bone cement," Bull. Mater. Sci (2000) 23(2):135-140.

Machine Translation of JP 1139516 (HO6(1994)-0842898) from http://www4.ipdl.inpit.go.jp/Tokujitu/tisogodbenk.ipdl, last viewed on Jan. 22, 2009.

Nilsson et al., "Biodegradation and biocompatability of a calcium sulphate-hydroxyapatite bone substitute," J. of Bone & Joint Surgery (Br) (2004) 86-B:120-125.

Nilsson et al., "Characterization of a novel calcium phosphate/sulphate bone cement," J. Biomedical Materials Research (2002) 61(4), 600-607.

Nilsson et al., "New Perspectives of Bioactives Calcium Phosphate Cements for Biomedical Applications," Research Centre in Biomedical Engineering, Dept. of Material Science and Metallurgy, Universitat Politecnica de Catalunya, Avda, Diagonal 647k Barcelona, E-08028, Spain, pp. 95-99, Nov. 2000.

Notice of Allowance dated Apr. 25, 2008 in related U.S. Appl. No. 10/333,026.

Office Action dated Jul. 2, 2008 in related U.S. Appl. No. 10/257,561.

Office Action dated Jul. 22, 2008 in related U.S. Appl. No. 10/499,023.

Office Action dated Mar. 21, 2006 in related U.S. Appl. No. 10/333,026.

Office Action dated Mar. 28, 2007 in related U.S. Appl. No. 10/257,561.

Office Action dated Oct. 10, 2007 in related U.S. Appl. No. 10/333,026.

Office Action dated Oct. 15, 2007 in related U.S. Appl. No. 10/257,561.

Office Action dated Oct. 31, 2006 in related U.S. Appl. No. 10/333,026.

Office Action dated Oct. 4, 2007 in related U.S. Appl. No. 10/499,023.
Office Action dated Sep. 5, 2006 in related U.S. Appl. No. 10/257,561.
Written Opinion of the International Searching Authority for PCT/SE2004/001626 dated Feb. 28, 2005.
Written Opinion of the International Searching Authority for PCT/SE2005/000932 dated Oct. 10, 2005.
Cahn, R.W., ed. *Materials Science and Technology: A Comprehensive Treatment*, 1992, vol. 14, VCH, Weinheim, pp. 70-109.
Elliott, J. C. "Chapter 1: General Chemistry of the Calcium Orthophosphates," in *Structure and Chemistry of the Apatites and Other Calcium Orthophosphates*, 1994, Elsevier: Netherlands.
English-language translation of ES 2 178 556 A1, "Calcium sulfate cement capable of controlled biodegradation."
De Robertis et al., "Solubility of some calcium-carboxylic ligand complexes in aqueous solution," Talanta 45 (1995)1651-1662.
English language translation of Japanese Office Action mailed on Jun. 1, 2010 in Japanese Application No. 2006-539432 related to U.S. Appl. No. 10/578,734.
Office Action in copending U.S. Appl. No. 10/257,561, filed Apr. 27, 2010.
Office Action in copending U.S. Appl. No. 10/499,023, filed Jun. 10, 2010.
Office Action in copending U.S. Appl. No. 10/547,671, filed May 5, 2010.
Office Action in copending U.S. Appl. No. 11/587,313, filed Jun. 18, 2010.
Office Action in copending U.S. Appl. No. 12/219,542, filed Jun. 25, 2010.
Office Action in copending U.S. Appl. No. 12/219,543, filed Mar. 19, 2010.
Office Action in copending U.S. Appl. No. 10/257,561, filed Nov. 10, 2009.
Office Action in copending U.S. Appl. No. 12/122,873, filed Mar. 19, 2010.
Office Action in copending U.S. Appl. No. 12/122,873, filed Oct. 29, 2009.
Office Action in copending U.S. Appl. No. 12/219,542, filed Jan. 11, 2010.
Starling, S., "EFSA Says Clacium Sulphate Safe in Supplements", 2008, Nutraingredients.com, 4 pages.
Technical Specification, Calcium Suolfate Hemihydrate Food Grade, 2009, 1 page.
Office Action in copending U.S. Appl. No. 10/547,671 dated Aug. 16, 2010 15 pages.
Office Action in copending U.S. Appl. No. 12/122,873 dated Sep. 8, 2010 8 pages.
Office Action in copending U.S. Appl. No. 12/219,542 dated Oct. 18, 2010 9 pages.
Office Action in copending U.S. Appl. No. 12/219,543 dated Sep. 8, 2010 7 pages.
Copending U.S. Appl. No. 12/911,198, filed Oct. 25, 2010 (47 pages).
Copending U.S. Appl. No. 12/911,266, filed Oct. 25, 2010 (47 pages).
English language translation of Japanese Office Action dated Sep. 9, 2010 in Japanese Application No. 2006-507949 related to U.S. Appl. No. 10/547,671 (4 pages).
Machine Translation of JP-A-2002-058736 (15 pages).
English Language Abstract of JP 2001-517997 T (1 page).
English Language Abstract of JP 2002-325831 A (1 page).
English Language Abstract of JP 2935708 B2 (1 page).
Office Action in copending U.S. Appl. No. 10/499,023 dated Apr. 17, 2009 (22 pages).
Office Action in copending U.S. Appl. No. 10/257,561 dated Apr. 3, 2009 (17 pages).
Office Action in copending U.S. Appl. No. 10/499,023 dated Sep. 9, 2009 (32 pages).
Notice of Allowance in copending U.S. Appl. No. 10/257,561 dated Feb. 23, 2011 (8 pages).
Notice of Allowance in copending U.S. Appl. No. 11/587,313 dated Jan. 26, 2011 (16 pages).
Office Action and English language translation thereof for Japanese Patent Application 2001-574164, corresponding to U.S. Appl. No. 10/257,561 dated Feb. 2, 2011 (10 pages).

* cited by examiner

DEVICE FOR PROVIDING SPONGY BONE WITH BONE SUBSTITUTE AND/OR BONE REINFORCING MATERIAL, BONE SUBSTITUTE AND/OR BONE REINFORCING MATERIAL AND METHOD

FIELD OF THE INVENTION

The present invention relates to a device for providing spongy bone with bone substitute and/or bone reinforcing material, wherein at least one perforating device is provided for making at least one hole in the spongy bone and wherein at least one flushing or rinsing device is provided for flushing or rinsing the hole with a rinsing agent. The invention further relates to a bone substitute and/or bone reinforcing material and a method.

BACKGROUND OF THE INVENTION

Vertebroplasty is a technique according to which biocompatible material is injected into a spongy vertebra. After some time, the injected material hardens, whereby an inner support is obtained for fixing the vertebra and thereby alleviate pain and reduce the risk of vertebral collapse.

The material is injected into the vertebra through a needle and in doing so, it is necessary to subject the material to high pressure, often one or more MPa. Hereby, there is an obvious risk that tissue material, e.g. blood and fat, in the vertebra is pressed out into the blood vessels or into fracture gaps such that said material can affect adjacent nerves. There is also an obvious risk that the injected material is pressed out into fracture gaps or into adjacent tissue. This is well known and the material and fat being pressed out can reach the blood vessels and the lungs, resulting in a poorer oxygenation, blood pressure reduction and, in exceptional cases, death.

By inserting an extra needle into the vertebra, the risk of leakage (note publications in the enclosed reference list, point 1 and 2, in the end of the description). Normally, this extra needle is left open or preferably connected to a suction hose for generating a suction effect (note publication in the enclosed reference list, point 3). However, any decisive effect is not reached with the prior art.

Various hole making and rinsing devices for making holes in and rinsing of vertebrae are known from e.g. U.S. Pat. No. 6,440,138, U.S. Pat. No. 6,716,216, U.S. Pat. No. 6,719,761 and U.S. Pat. No. 6,740,090, but none of these publications describes generation of a vacuum in the vertebrae for providing safe suction of bone substitute and/or bone reinforcing material into said vertebrae.

SUMMARY OF THE INVENTION

The object of the present invention has been to eliminate the abovementioned problem and this is arrived at while the invention has been given the characterizing features of each of subsequent claims 1, 44, 51, 53, 56 and 58.

By making a hole in the spongy bone and rinse it, tissue material and other material can be flushed away from the hole and the sides thereof, such that said sides get rough or uneven surfaces with depressions into which the bone substitute and/ or bone reinforcing material can be brought to penetrate by generating a vacuum in the hole and without risking that said bone substitute and/or bone reinforcing material penetrates into the blood paths.

BRIEF DESCRIPTION OF THE DRAWINGS

The invention will be further described below with reference to the accompanying drawings, in which.

DESCRIPTION OF EXAMPLE EMBODIMENTS

Figure 1:
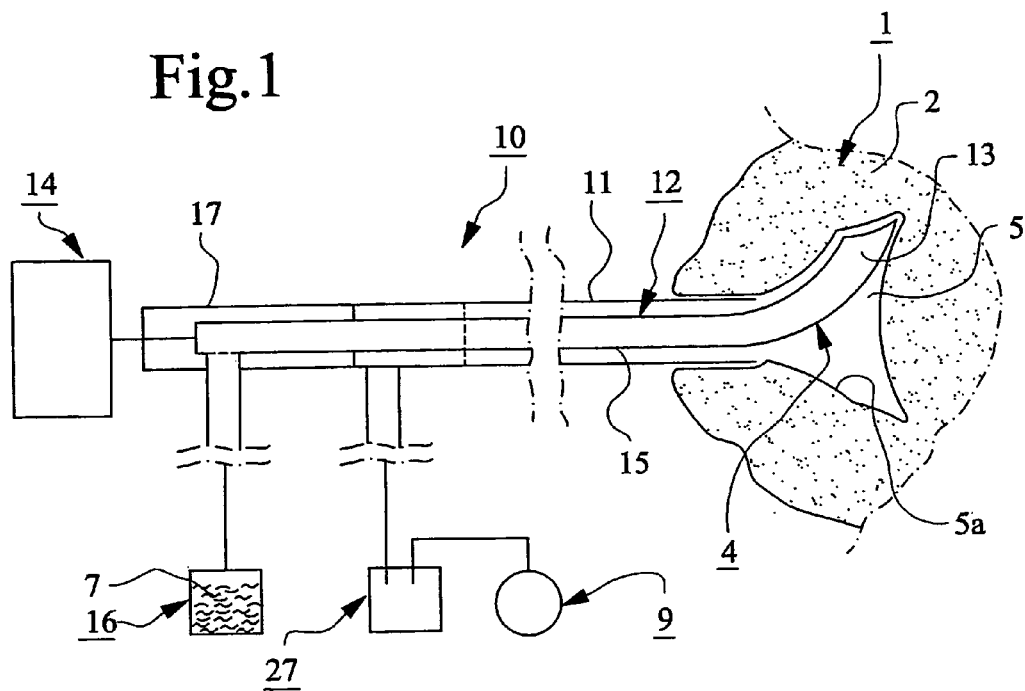
FIG. 1 is a schematic view of a device according to the invention when making a hole in a spongy vertebra shown in section.

In the figures, different parts of a device for preparing spongy bone 1, e.g. a vertebra 2, to receive bone substitute and/or bone reinforcing material 3, and for locating said material in said vertebra is schematically illustrated. Said device comprises at least one perforating device 4 for making at least one hole 5 in the vertebra 2, at least one flushing or rinsing device 6 for flushing or rinsing said hole with rinsing agent 7 and at least one supply device 8 which permits suction and/or insertion of bone substitute and/or bone reinforcing material 3 into the vertebra.

At least one vacuum source 9 is provided to generate a vacuum in the hole 5 in the vertebra 2 for sucking and/or facilitate insertion of bone substitute and/or bone reinforcing material 3 into said vertebra.

Figure 2:
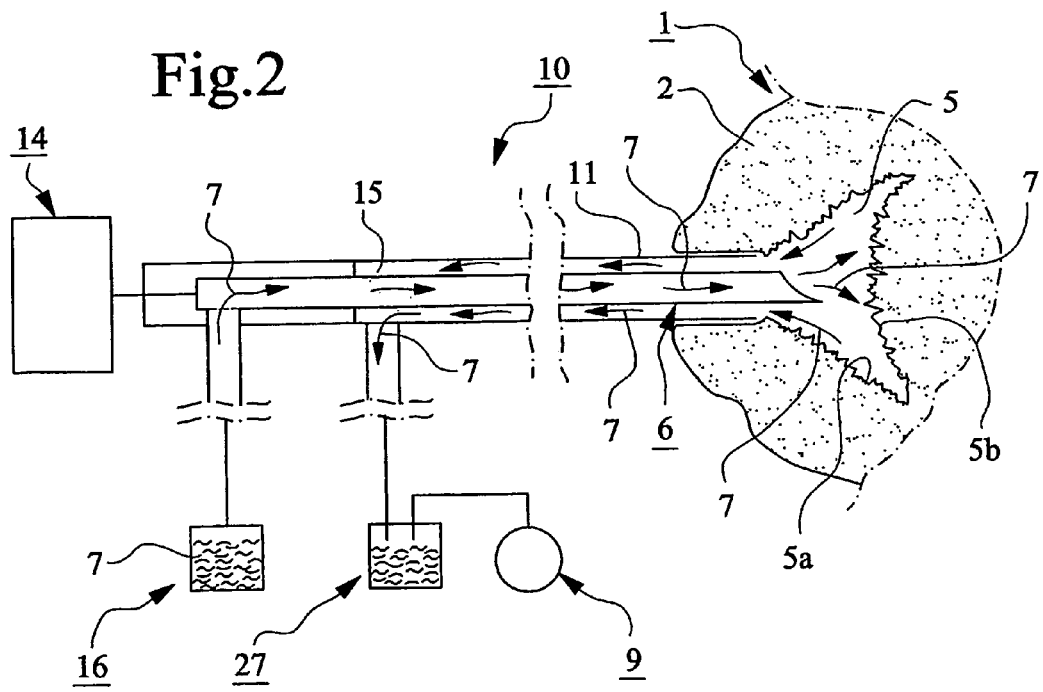
FIG. 2 illustrates parts of the device of FIG. 1 during flushing or rinsing of the hole made in the spongy vertebra.

The perforating device 4 can be designed in many different ways and so can also the rinsing device 6. At the exemplary embodiment of FIGS. 1 and 2, the perforating and rinsing devices 4, 6 are combined to a device 10 including an outer tube member 11 which can be located at the vertebra 2. In the tube member 11 there is provided a perforating means 12 which is movable relative to said tube member in coaxial and/or rotary direction. The perforating means 12 has and/or cooperates with a perforating member 13 which can be designed in many ways. As an example of a perforating member 13, it is shown an end portion of the perforating means 12 which can be retracted into the outer tube member 11 when this is located at the vertebra 2 and which is bent when it is expelled out of said pipe member. When the perforating means 12 is rotated, the bent perforating member 13 will make the hole 5 in the vertebra 2.

The movements of the perforating means 12 can be obtained by means of a drive unit 14 of a suitable type.

Figure 3:
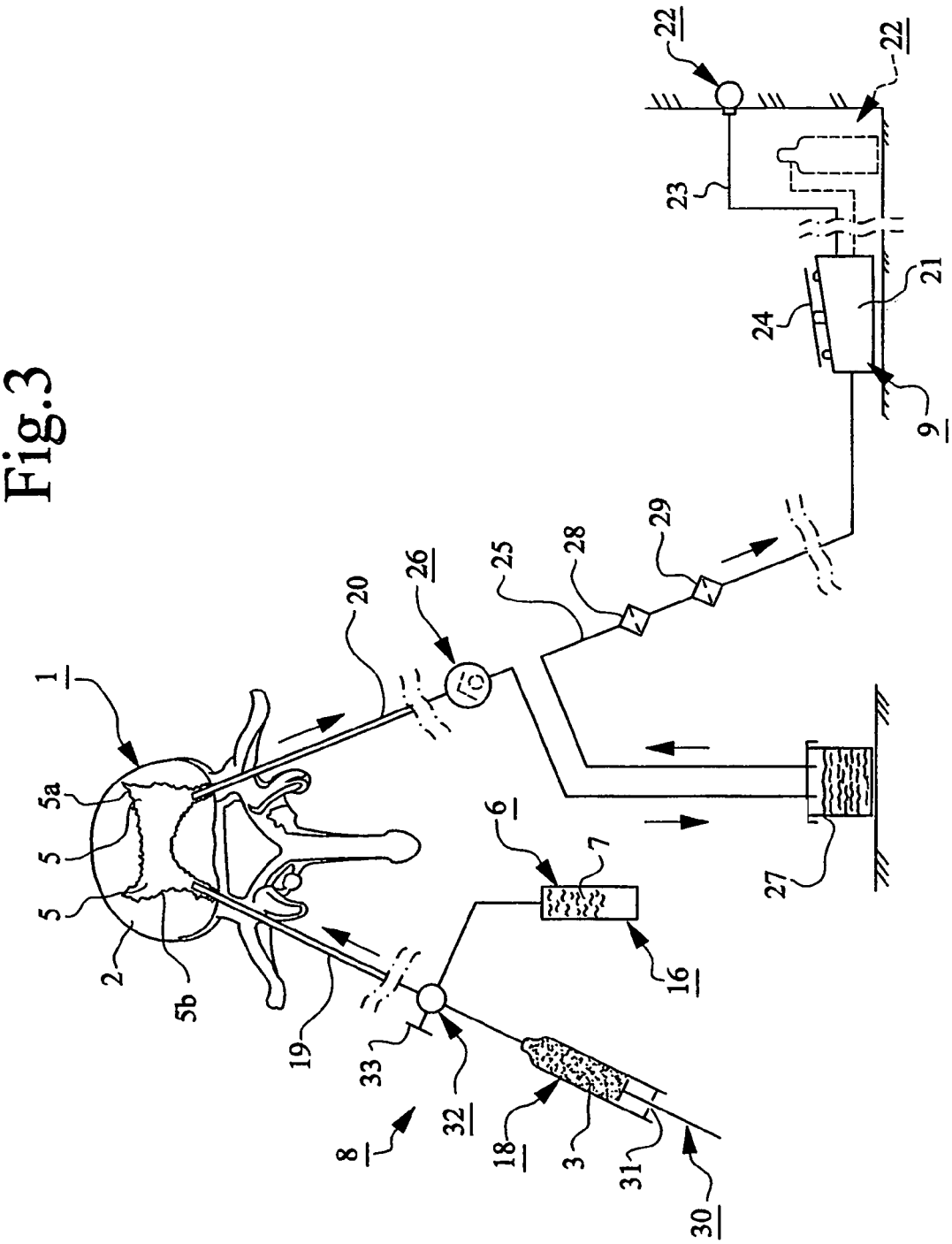
FIG. 3 illustrates parts of the device according to the invention during suction of bone substitute and/or bone reinforcing material into the vertebra.

At the exemplary embodiment, the perforating means 12 is designed as an inner tube member 15. A rinsing agent container 16 is connected to this inner tube member 15 through a connecting device 17 which permits feeding of rinsing agent 7 from the container 16 into the inner tube member 15 irrespective of whether said inner tube member is rotatable or not. Alternatively, the rinsing agent container 16 may be connected to the outer tube member 11 and the collecting device 27 and the vacuum source 9 to the inner tube member 15, such that the outer tube member 11 can lead rinsing agent 7 into the hole 5 and be sucked out of said hole through the inner tube member 15. The perforating device 4 is used preferably for making at least two holes 5 in the vertebra 2. These holes 5 are located such that they communicate with each other either by extending into each other (as is illustrated in FIG. 3) or by having spongy bone 1 between them since such bone is pervious to air and can be provided with bone substitute and/or bone reinforcing material 3.

The vacuum source 9 is provided to suck rinsing agent 7 through the hole 5 and it is preferably connected to the outer tube member 11 for sucking, through said outer tube member, rinsing agent 7 and tissue material and other material out of said hole 5.

Between the outer tube member 11 and the vacuum source 9 there is preferably a collecting device 27 for collecting rinsing agent 7 and tissue material and other material brought along therewith out of the hole 5.

The rinsing device 6 is preferably provided also to flush or rinse the sides 5a of the hole 5 such that depressions 5b and similar are formed therein while tissue material and other material is flushed off said sides. This is advantageous since bone substitute and/or bone reinforcing material 3, by means of the vacuum generated in the hole 5, can be brought to penetrate into the depressions 5b.

At the embodiment illustrated in FIG. 3, the outer tube member 11 has its equivalent in a first cannula or needle 19 which can cooperate with a perforating device (not shown) for making a first hole 5 in the vertebra 2. A second cannula or needle 20 is connected to a vacuum source 9 and this second cannula can also cooperate with a perforating device (not shown) for making a second hole 5 in the vertebra 2.

The supply device 8 illustrated in FIG. 3 may have a container 18 for mixing various components for production of bone substitute and/or bone reinforcing material 3 and/or for storage thereof. The container 18 is connected or connectable to a first cannula or needle 19 which can be inserted into the vertebra 2 and which is adapted to lead bone substitute and/or bone reinforcing material 3 into the holes 5 in the vertebra 2. A second cannula or needle 20 can be inserted into the vertebra 2 and is connected to the vacuum source 9, which is adapted to generate a vacuum in the holes 5 such that bone substitute and/or bone reinforcing material 3 is sucked into said holes and/or for facilitating insertion or feeding of said material into said holes.

The vacuum source 9 can be an injector pump 21 which is run or driven by a suitable compressed medium from a compressed-medium device 22. The injector pump 21 may e.g. be driven by compressed air and connected, through a compressed-air conduit 23, to a compressed-medium device 22 in the form of a compressed-air device. This device may be built into a hospital or other locality in which the injector pump 21 shall be used. Alternatively, the injector pump 21 can be run or driven by another commercially available gas as is indicated with broken lines in FIG. 3.

The compressed-medium device 22 can operate the injector pump 21 with a compressed-medium pressure of 4.5-8.5 bar and the injector pump 21 may be of a type which is placed on the floor and which has a foot pedal 24 for its operation. Thus, the injector pump 21 can be started by tilting the foot pedal 24 in one direction and stopped by tilting the foot pedal 24 in the opposite direction. As an example of a usable injector pump 21 in this connection one can mention an injector pump of the type used for producing bone cement as defined in U.S. Pat. No. 5,328,262 and sold under the product name Scan Vacuum Pumps™ by the company Scandimed International AB, Sjöbo, Sweden.

The injector pump 21 is preferably provided to generate a vacuum in all the holes 5 of the spongy bone 1 such that said holes are filled or can be filled with bone substitute and/or bone reinforcing material 3 and/or a vacuum such that the bone substitute and/or bone reinforcing material 3 is distributed therein, preferably without any or any substantial portions thereof being sucked into the second cannula 20.

The injector pump 21 can be provided to generate a vacuum of between −0.5 bar and −0.92 bar in the spongy bone 1, which vacuum corresponds to a 70% and 90% absolute vacuum. In many cases it is sufficient that the injector pump 21 generates a vacuum of between −0.7 bar and −0.8 bar in the spongy bone 1.

The injector pump 21 is preferably provided to suck tissue material such as blood and fat out of the holes 5 of the spongy bone 1 and into the second cannula 20 before bone substitute and/or bone reinforcing material 3 is sucked into the spongy bone 1 through the first cannula 19.

In at least one connecting conduit 25 between the second cannula 20 (the inlet end of which is the end which is inserted into a hole 5 of the spongy bone 1) and the injector pump 21, there may be provided a non-return valve device 26 and/or a collecting device 27 and/or a monomer filter 28 (if the bone substitute and/or bone reinforcing material 3 is of bone cement type) and/or a bacteria filter 29.

The collecting device 27 may be a container which is placed on the floor and closed or sealed by means of a cap. A portion of the connecting conduit 25, which is connected to the second cannula 20, is directed through the cap and a small distance down into the container. Another portion of the connecting conduit 25 is also directed through the cap and a small distance down into the container. When tissue material is sucked from the holes 5 of the spongy bone 1 to the collecting device 27, said material is collected down below in the container and is therefore prevented from being sucked further towards the injector pump 21 and into said pump. If there is a monomer filter 28 and/or a bacteria filter 29 between the collecting device 27 and the injector pump 21, the tissue material is prevented also from being sucked thereto.

The monomer filter 28 may be a carbon filter and is adapted to prevent monomer gases, generated during production of bone substitute and/or bone reinforcing material 3 in the form of bone cement, from being sucked into the injector pump 21 and discharged to the surroundings. The advantages with such a monomer filter 28 are described in the publication according to the enclosed reference list, point 4. The bacteria filter 29 is provided to prevent bacteria from entering or getting into the holes 5 of the spongy bone 1 if the connecting conduit 25 is opened or opens unintentionally and air is sucked therethrough to the holes 5 if there is a vacuum therein.

The monomer filter 28 and bacteria filter 29 may be provided in that portion of the connecting conduit 25 which connects the collecting device 27 with the injector pump 21.

The non-return valve device 26, which preferably can be provided in the connecting conduit 25 between the collecting device 27 and the second cannula 20, is adapted to prevent tissue material from being sucked out of the collecting device 27 and into the holes 5 of the spongy bone 1 if the connecting conduit 25 is opened or opens unintentionally such that a suction is generated therein towards the holes 5 of the spongy bone 1 if there is a vacuum therein.

The container 18 may include a feeding device 30 for feeding bone substitute and/or bone reinforcing material 3 out of the container 18 and into the holes 5 of the spongy bone 1 at the same time the injector pump 21 generates a vacuum therein or thereafter.

The feeding device 30 is schematically illustrated with a feed means 31 which is displaceably mounted relative to the container 18 and which can be displaced manually for discharge of bone substitute and/or bone reinforcing material 3 from the container 18 and through the first cannula 19 into the holes 5 of the spongy bone 1.

The container 18 may eventually be used as mixing container for mixing the components required for the production of such bone substitute and/or bone reinforcing material 3 that can be brought to harden after insertion thereof into the holes 5 of the spongy bone 1. This mixing can occur with a mixing means or in any other way. Such a mixing means can preferably be moved manually back and forth in the container 18 and is eventually rotated relative thereto for mixing the components.

A valve device 32 may be provided for, on one hand, close or interrupt the supply of bone substitute and/or bone reinforcing material 3 through the first cannula 19 to the holes 5 of the spongy bone 1 until the injector pump 21 has generated a suitable vacuum therein. When this is done, the valve device 32 may be opened for permitting suction of bone substitute and/or bone reinforcing material 3 into the holes 5 of the spongy bone 1 by means of the injector pump 21. The valve device 32 may be located on the first cannula 19 or on a connecting conduit between the container 18 and the first cannula 19. The valve device 32 may be manually operable by means of a control handle 33.

As an alternative to the embodiment of the flushing or rinsing device 6 described above, said device may be combined with the supply device 8. At this alternative, the rinsing agent container 16 of the rinsing device 6 may be connected to the first cannula 19 e.g. through the valve device 32 which in this case can be a three way valve permitting either that the supply of rinsing agent to the vertebra 2 is open and the supply of bone substitute and/or bone reinforcing material 3 to the vertebra 2 is closed or that said supply of rinsing agent is interrupted and said supply of material open.

The rinsing agent 7 may be of different types and it may e.g. be distilled water or a sodium chloride solution and/or be detergent and/or include at least one trombolytic substance, e.g. heparin, streptokinase, urokinase, TPA and/or other substances dissolving coagulum and thrombi.

The bone substitute and/or bone reinforcing material 3 may consist of primarily minerals or ceramics which can be mixed with a hardener, e.g. water. These substances may be selected from the group comprising calcium sulphate-α-hemihydrate, calcium sulphate-β-hemihydrate, calcium sulphate-dihydrate, calcium carbonate, α-tricalcium phosphate, hydroxyapatite, dicalcium phosphate-dihydrate, anhydrous dicalcium phosphate, tetracalcium phosphate, β-tricalcium phosphate, calcium deficient hydroxyapatite, monocalcium phosphate-monohydrate, mono-calcium phosphate, calcium-pyurophosphate, precipitated hydroxyapatite, carbonaceous apatite (dahlite), octa-calcium phosphate, amorphous calcium phosphate, oxyapatite, carbonate apatite and calcium aluminate.

A ceramic material may be calcium aluminate, which forms part of the product Doxa T from the company Doxa (www.doxa.se/pdf/nyhet_1.pdf).

X-ray contrast agents can be added to said ceramic bone substitute and/or bone reinforcing material 3, e.g. water soluble non-ionic X-ray contrast agents selected from the group comprising iohexol, ioversol, iopamidol, iotrolan, metrizamide, iodecimol, ioglucol, ioglucamide, ioglunide, iogulamide, iomeprol, iopentol, iopromide, iosarcol, iosimide, iotusal, ioxilan, iofrotal and iodecol.

Alternatively, the bone substitute and/or bone reinforcing material 3 can be a hardenable bone cement comprising polymer and monomer components. The polymer may be polymethylmethacrylate (PMMA) and the monomer methylmethacrylate (MMA). A polymer base material can be the product Cortoss™ from the company Orthovita in the U.S. For composition see www.orthovita.com/products/cortoss/oustechspecs.html. Another polymer base material can be the product SECOUR® Acrylic Resin PMMA from parallax medical inc. (www.parallax-medical.com/go/9192b550-5642-1157-a432-d7a2b98310fe).

The bone substitute and/or bone reinforcing material 3 may consist of a mineral and/or a ceramic in combination with polymer material.

Figure 4:
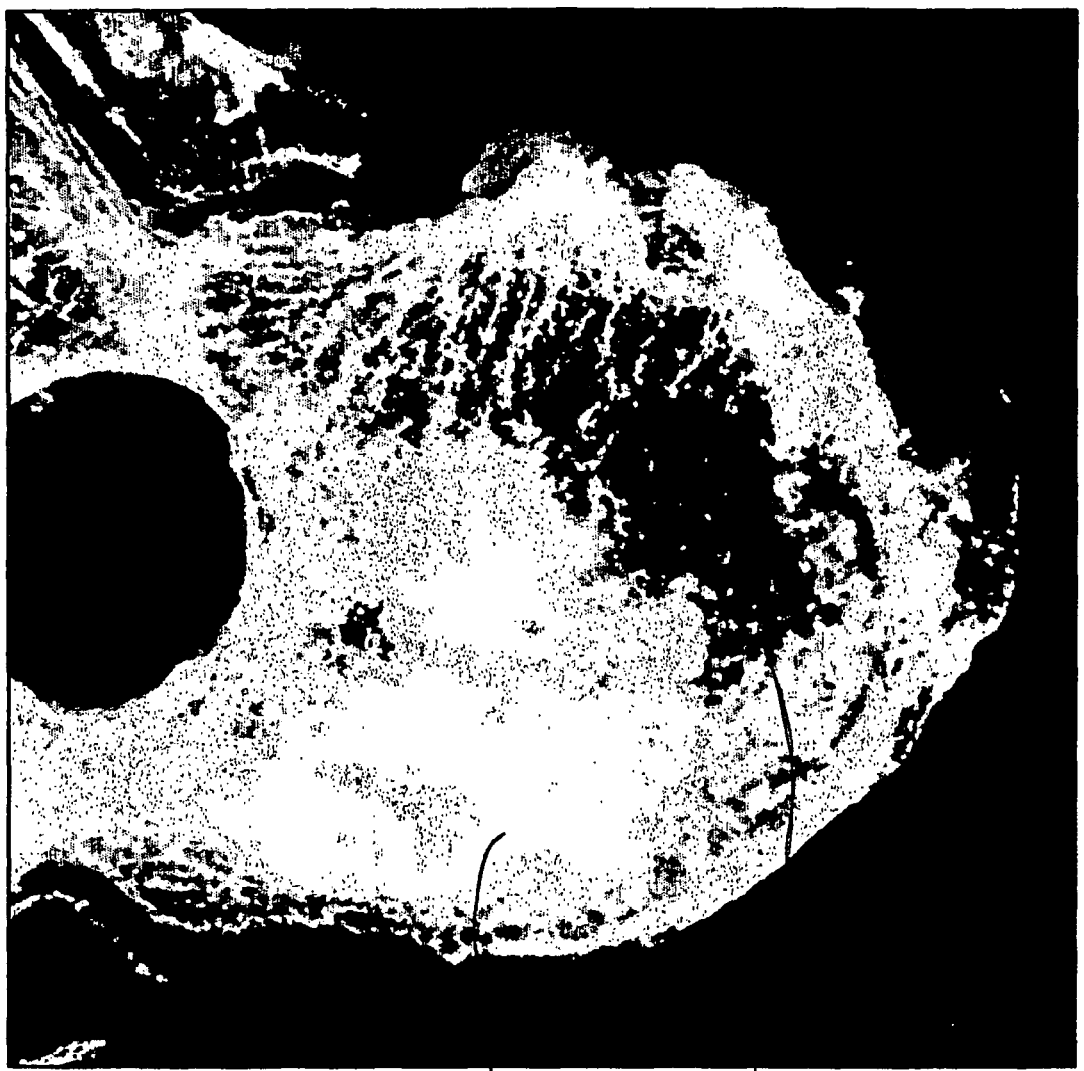
FIG. 4 is a sectional view of a spongy vertebra in which bone substitute and/or bone reinforcing material has been injected with pressure through a needle according to prior art.
Figure 5:
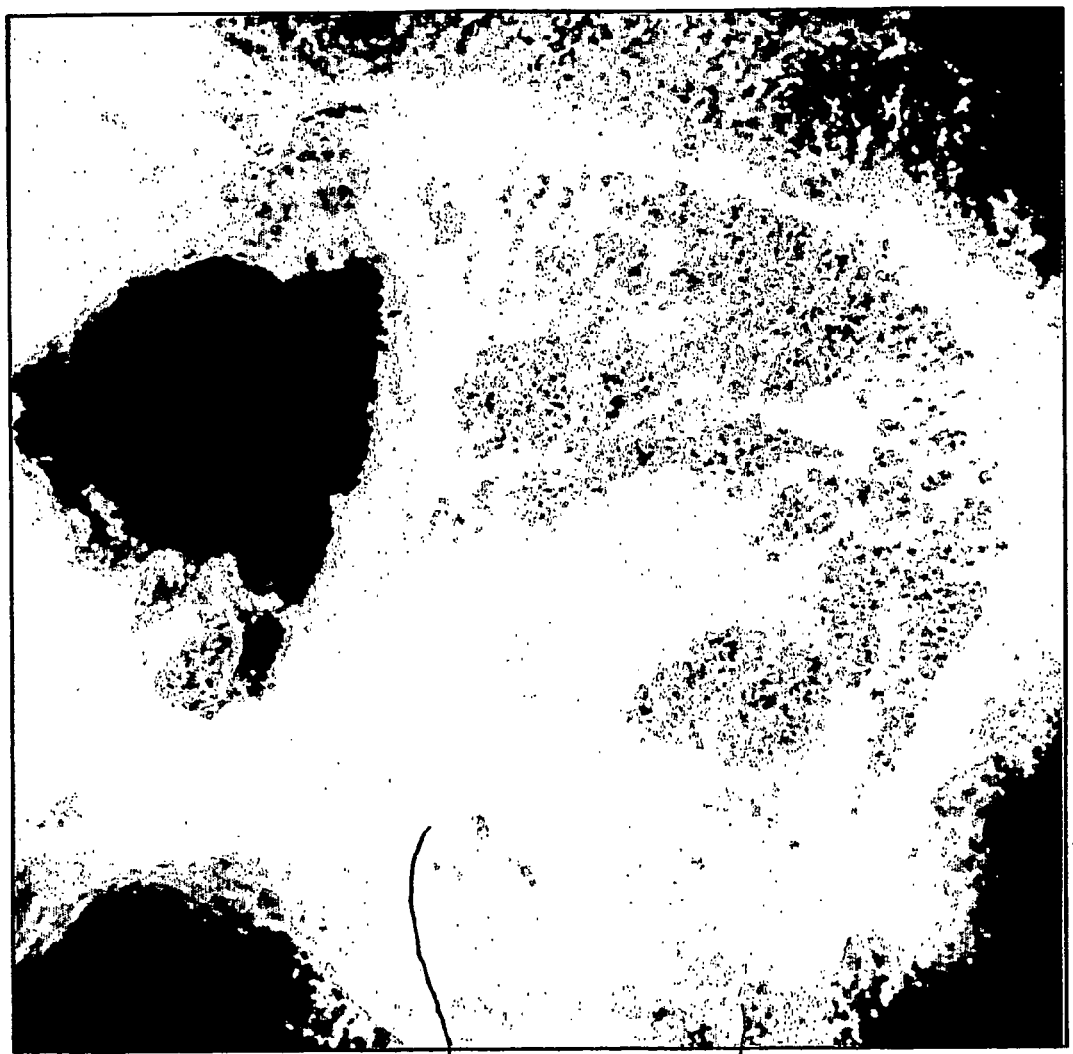
FIG. 5 is a sectional view of a spongy vertebra into which bone substitute and/or bone reinforcing material has been sucked by means of a device according to the invention.

The advantages with the invention is obvious when comparing the degree or ratio of fullness of the vertebra 2 of FIGS. 4 and 5. In the vertebra 2 of FIG. 4, the bone substitute and/or bone reinforcing material 3 has been pressed into said vertebra 2 through a cannula or needle and it clearly appears from FIG. 4 that only a part of the vertebra 2 is filled with bone substitute and/or bone reinforcing material 3. In the vertebra 2 of FIG. 5 however, the bone substitute and/or bone reinforcing material 3 has been sucked into the vertebra 2 in accordance with the invention through the cannula or needle and it is clearly evident from FIG. 5 that substantially larger parts of the vertebra 2 are filled with bone substitute and/or bone reinforcing material 3 without said material having been pressed out into the blood paths.

It is also obvious from FIG. 5 that the negative pressure generated by the vacuum source 9 has provided for a uniform and complete distribution of the bone substitute and/or bone reinforcing material 3 in the hole 5 and depressions 5b in the sides 5a of the hole 5.

The invention is not limited to what is described above and illustrated in the drawings, but may vary within the scope of subsequent claims. Thus, the vacuum source 9 may instead of an injector pump 21 be another vacuum pump which can be electrically operated or operated by gas or by hand or operated in any other way, that the hole 5 may be more than one hole and surrounding parts thereto, that the rinsing agent 7 may be another than those described and that the bone substitute and/or bone reinforcing material 3 may be of another type than those described.

There may be a device for imparting pulse like suction and/or insertion movements to the bone substitute and/or bone reinforcing material 3 into the hole(s) 5 in the spongy bone 1. Furthermore, there may be a device for imparting reciprocating suction and/or insertion movements to the bone substitute and/or bone reinforcing material 3 into the hole(s) 5 in the spongy bone 1.

There may also be a device for pulse like suction and/or feeding of the rinsing agent 7 through the hole(s) 5 in the spongy bone 1.

Said device may be defined by pulsating the vacuum source 9 and/or its vacuum generation and/or by generating pulses by means of the feeding device 30.

REFERENCE LIST

1) Aebli N, Krebs J, Schwenke D, Davis G. Theis J C. Cardiovascular charges during multiple vertebroplasty with and without vent-hole: an experimental study in sheep. Spine 2003; 28(14):1504-11.
2) Koessler M J, Aebli N, Pitto R P. Fat and Bone Marrow Embolism During Percutaneous Vertebroplasty. Anesth Analg 2003; 97:293-294.
3) Lidgren, Lars. Bone Substitutes. Karger Gazette No. 65 2003; Bone and Joints.
4) Kirby B S, Doyle A, Gilula L A. Acute bronchospasm due to exposure to polymethacrylate vapours during percutaneous vertebroplasty. AJR J Roentgenol. 2003 February; 180 (2):543-4.

The invention claimed is:

1. A system for providing spongy bone with bone substitute and/or bone reinforcing material, including:

at least one perforating device (4) configured to make at least one hole (5) in the spongy bone (1), at least one flushing or rinsing device (6) configured to flush or rinse the hole (5) with a rinsing agent (7), at least one supply device (8) configured to supply the bone substitute and/or bone reinforcing material (3) to the hole (5) in the spongy bone (1), and at least one vacuum source (9) configured to generate a vacuum in the hole (5) in the spongy bone (1), suck the rinsing agent (7) into the hole (5) in the spongy bone (1), and to suck rinsing agent (7) and tissue material out of said hole (5), wherein said vacuum source (9) is further configured to suck the bone substitute and/or bone reinforcing material (3) into the hole (5) in the spongy bone (1) from the supply device, and wherein said vacuum source (9) is configured to generate a vacuum of between −0.5 bar and −0.92 bar in the hole (5) of the spongy bone (1).

2. The system according to claim 1, wherein the vacuum source (9) is configured to generate a vacuum in the hole (5) of the spongy bone (1) such that the bone substitute and/or bone reinforcing material (3) is sucked into said hole (5) and distributed therein without substantial portions thereof being sucked out of the hole (5).

3. The system according to claim 1, wherein a collecting device (27) is configured to collect tissue material that has been sucked out of the hole (5) of the spongy bone (1) by the vacuum source (9) thereby preventing tissue material from being sucked into one or more of the vacuum source (9), monomer filter (28), and a bacteria filter (29).

4. The system according to claim 1, further comprising a monomer filter (28) configured to prevent poisonous gases, which are generated during production of bone substitute and/or bone reinforcing material (3), from being discharged into the surroundings.

5. The system according to claim 1, further comprising a bacteria filter (29) configured to prevent bacteria from getting into the hole (5) of the spongy bone (1) if a connection between the vacuum source (9) and the spongy bone (1) is opened unintentionally.

6. The system according to claim 1, further comprising a non-return valve device (26) configured to prevent tissue material and/or any other material and/or bacteria from being sucked into the hole (5) of the spongy bone (1) if the connection between the vacuum source (9) and the hole (5) in the spongy bone (1) is opened unintentionally.

7. The system according to claim 3, further including a non-return valve device (26) configured to be located between the hole (5) in the spongy bone (1) and the collecting device (27).

8. The system according to claim 3, further including a non-return valve device (26) configured to be located between the monomer filter (28) and/or bacteria filter (29) and the hole (5) in the spongy bone (1).

9. The system according to claim 1, further including container (18) configured to produce and/or store bone substitute and/or bone reinforcing material (3), wherein the container (18) includes a feeding device (30) configured to feed bone substitute and/or bone reinforcing material (3) out of the container (18) and into the hole (5) of the spongy bone (1) at the same time the vacuum source (9) generates a vacuum therein.

10. The system according to claim 1, further including container (18) configured to produce and/or store bone substitute and/or bone reinforcing material (3), wherein the container (18) includes a feeding device (30) configured to feed bone substitute and/or bone reinforcing material (3) into the hole (5) of the spongy bone (1) after the vacuum source (9) has generated a vacuum therein.

11. The system according to claim 9, wherein the feeding device (30) is manually operable.

12. The system according to claim 1, wherein the vacuum source (9) is configured to generate a vacuum of between −0.7 and −0.8 bar in the hole (5) of the spongy bone (1).

13. The system according to claim 1, further comprising a valve device (32) configured to close or interrupt the supply of bone substitute and/or bone reinforcing material (3) to the hole (5) of the spongy bone (1) until the vacuum source (9) has generated a suitable vacuum therein, the valve device (32) being configured to open and permit supply of bone substitute and/or bone reinforcing material (3) into the hole (5) of the spongy bone (1) via suction when said suitable vacuum has been measured therein.

14. The system according to claim 1, further comprising at least a first cannula or needle and a second cannula or needle (19, 20) configured to be insertable into the spongy bone (1) such that they are simultaneously directed into the hole (5) thereof, wherein the first cannula or needle (19) is connected to a container (18) for producing and/or storing the bone substitute and/or bone reinforcing material (3) while the second cannula or needle (20) is connected to the vacuum source (9).

15. The system according to claim 14, wherein the flushing or rinsing device (6) comprises a rinsing agent container (16) which is connected to the first cannula or needle (19) and is configured to direct rinsing agent (7) into the hole (5) of the spongy bone (1) through said first cannula (19) and out of said hole (5) to the second cannula or needle (20).

16. The system according to claim 15, wherein a valve device (32) is configured to either open for supply of bone substitute and/or bone reinforcing material (3) or of rinsing agent (7) through the first cannula or needle (19).

17. The system according to claim 1, wherein the rinsing device (6) is configured to form depressions (5b) on the sides (5a) of the hole (5) by flushing or rinsing the sides (5a) of the hole (5) to remove tissue material and/or other material, and wherein the depressions may be configured to receive bone substitute and/or bone reinforcing material.

18. The system according to claim 1, wherein the perforating device (4) includes:
an outer tube member (11) located at the spongy bone (1); and
a perforating means (12), wherein the perforating means (12) is configured to be movable in said outer tube member (11) in coaxial and/or rotary direction and includes and/or cooperates with a perforating member (13) for making the hole (5) in the spongy bone (1).

19. The system according to claim 18, wherein the perforating means (12) further includes an inner tube member (15) configured to direct rinsing agent (7) into or out of the hole (5) in the spongy bone (1).

20. The system according to claim 19, wherein the outer or inner tube member (11 or 15) is connected to a vacuum source (9) for sucking rinsing agent (7) through the hole (5) in the spongy bone (1) and out of said hole through the other tube member (11).

21. The system according to claim 1, wherein the perforating device (4) further includes several units configured to make at least two holes (5) in the spongy bone (1), wherein the at least two holes (5) are configured to either extend into each other, or be separated from one another with spongy bone (1) remaining therebetween, wherein the spongy bone (1)

remaining between the at least two holes (5) is penetrated by air and provided with bone substitute and/or bone reinforcing material (3).

22. The system according to claim 1, wherein the vacuum source (9) is an injector pump (21) operable by a compressed medium.

23. The system according to claim 22, wherein the injector pump (21) is connected to a compressed-medium device (22) which is designed as a compressed-air device and is positionable in localities in or close to which the vacuum source (9).

24. The system according to claim 23, wherein the injector pump (21) is connected to a compressed-medium device (22) with commercial gas.

25. The system according to claim 23, wherein the injector pump (21) is connected to a compressed-medium device (22) which is configured to operate said pump with a compressed-medium pressure of 4.5-8.5 bar.

26. The system according to claim 1, wherein the vacuum source (9) is an electrically operated vacuum pump.

27. The system according to claim 1, wherein the vacuum source (9) is a pump operated by gas.

28. The system according to claim 1, wherein the vacuum source (9) is operated by hand.

29. The system according to claim 1, wherein the spongy bone (1) is a spongy vertebra (2).

30. The system according to claim 1, wherein the spongy bone (1) is a fracture due to osteoporosis.

31. The system according to claim 1, wherein the spongy bone (1) is a femoral or knee fracture.

32. The system according to claim 1, wherein the rinsing agent (7) is a sodium chloride solution.

33. The system according to claim 1, wherein the flushing or rinsing device contains the rinsing agent, wherein the rinsing agent (7) contains a detergent.

34. The system according to claim 1, wherein the flushing or rinsing device contains the rinsing agent, wherein the rinsing agent (7) contains at least one trombolytic substance.

35. The system according to claim 1, wherein the flushing or rinsing device contains the rinsing agent, wherein the rinsing agent (7) is distilled water.

36. The system according to claim 1, further including a secondary device (9 and/or 30) configured to impart pulse like suction and/or insertion movements to the bone substitute and/or bone reinforcing material (3) into the hole (5) in the spongy bone (1).

37. The system according to claim 1, further including a secondary device (9 and/or 30) configured to impart reciprocating suction and/or insertion movements to the bone substitute and/or bone reinforcing material (3) into the hole (5) in the spongy bone (1).

38. The system according to claim 1, further including a secondary device (9 and/or 30) configured to impart for pulse like suction and/or feeding of the rinsing agent (7) through the hole (5) in the spongy bone (1).

39. The system according to claim 1, further including a bone substitute and/or bone reinforcing material, wherein the bone substitute and/or bone reinforcing material (3) is at least one of a mineral material, a substantially mineral material, a ceramic material, and a substantially ceramic material.

40. The system according to claim 39, wherein the mineral material or ceramic material is a hardenable mineral or ceramic which can be brought to harden in the spongy bone (1).

41. The system according to claim 40, wherein the mineral material or ceramic can be brought to harden by being mixed with a hardening agent.

42. The system according to claim 39, wherein the mineral material or ceramic is selected from the group comprising calcium sulphate-α-hemihydrate, calcium sulphate-β-hemihydrate, calcium sulphate-dihydrate, calcium carbonate, α-tricalcium phosphate, hydroxyapatite, dicalcium phosphate-di-hydrate, anhydrous dicalcium phosphate, tetracalcium phosphate, β-tricalcium phosphate, calcium deficient hydroxyapatite, monocalcium phosphate-monohydrate, mono-calcium phosphate, calcium-pyrophosphate, precipitated hydroxyapatite, carbonaceous apatite (dahlite), octacalcium phosphate, amorphous calcium phosphate, oxyapatite, carbonate apatite and calcium aluminate.

43. The system according to claim 39, wherein an X-ray contrast agent is mixed with the ceramic material.

44. The system according to claim 43, wherein the X-ray contrast agent is water soluble and non-ionic.

45. The system according to claim 44, wherein the water soluble, non-ionic X-ray contrast agent is selected from the group comprising iohexol, ioversol, iopamidol, iotrolan, metrizamide, iodecimol, iodecimol, ioglucol, ioglucamide, ioglunide, iogulamide, iomeprol, iopentol, iopromide, iosarcol, iosimide, iotusal, ioxilan, iofrotal and iodecol.

46. The system according to claim 1, further including a bone substitute and/or bone reinforcing material, wherein the bone substitute and/or bone reinforcing material (3) is a bone cement including a polymer and a monomer, wherein the polymer and monomer harden to bone cement after mixing with each other and after said sucking and/or insertion or feeding thereof into the spongy bone (1).

47. The system according to claim 46, wherein the bone substitute and/or bone reinforcing material (3) consists of mineral and/or ceramic in combination with polymer material.

48. The system according to claim 34, wherein the at least one trombolytic substance is chosen from heparin, streptokinase, urokinase, TPA, and other substances dissolving coagulum and thrombi, and mixtures thereof.

49. The system according to claim 46, wherein the components polymer is polymethyl-methacrylate (PMMA)-type, and the components monomer is methylmethacrylate (MMA)-type.

50. A method for providing spongy bone with bone substitute and/or bone reinforcing material, wherein:
   at least one hole (5) is made in the spongy bone (1) by at least one perforating device,
   the at least one hole (5) is flushed or rinsed with rinsing agent (7) by at least one flushing or rinsing device (6),
   the at least one hole (5) is supplied with bone substitute and/or bone reinforcing material by at least one supply device (8), and
   a vacuum is generated in the hole (5) for sucking and/or facilitating insertion or feeding of the bone substitute and/or bone reinforcing material (3) into the hole (5) by at least one vacuum source (9), such that the bone substitute and/or bone reinforcing material (3) is sucked into the hole (5) in the spongy bone (1), the vacuum generated is between −0.5 bar and −0.92 bar.

51. The method according to claim 50, wherein a vacuum is generated in the hole (5) for sucking rinsing agent (7) through said hole (5).

52. The method according to claim 50, wherein the rinsing agent (7) is brought to flush tissue material and other material away from the sides (5a) of the hole (5) such that depressions (5b) are formed therein and that bone substitute and/or bone reinforcing material (3) is brought to penetrate into said depressions (5b).

53. A method for providing spongy bone with bone substitute and/or bone reinforcing material (3) comprising, applying bone substitute material and/or bone reinforcing material (3) from at least one supply device (8) in at least one hole (5) in spongy bone (1) by generating a pulsating vacuum in the hole (5) by at least one vacuum source (9) such that the bone substitute and/or bone reinforcing material (3) is brought to pulsate during its application in the spongy bone (1), the vacuum generated is between −0.5 bar and −0.92 bar.

54. The method according to claim 53, wherein reciprocating movements are imparted to the bone substitute and/or bone reinforcing 22 material (3) during its application in the hole (5) in the spongy bone (1).

55. A method for providing spongy bone with bone substitute and/or bone reinforcing material (3) comprising:
   rinsing at least one hole (5) in spongy bone (1) with rinsing agent by at least one flushing or rinsing device, wherein the rinsing agent (7) is sucked pulsatingly through the hole (5) in the spongy bone (1) by generating a pulsating vacuum by at least one vacuum source (9) in said hole (5), such that the rinsing agent (7) is sucked into the hole (5) in the spongy bone (1), where the vacuum generated in the hole (5) is of between −0.5 bar and −0.92 bar,
   applying bone substitute and/or bone reinforcing material (3) from at least one supply device (8) in the hole (5) in the spongy bone (1) by generating a vacuum by the at least one vacuum source (9).

56. A system for providing spongy bone with bone substitute and/or bone reinforcing material, including:
   at least one supply device (8) configured to permit the supply of bone substitute and/or bone reinforcing material (3) to a hole (5) in a spongy bone (1); and
   at least one vacuum source (9) configured to generate a vacuum in the hole (5) in the spongy bone (1), and suck the bone substitute and/or bone reinforcing material (3) from the at least one supply device (8) into the hole (5) in the spongy bone (1);
   wherein the vacuum source (9) is configured to generate a vacuum of between about −0.5 bar and about −0.92 bar in the hole (5) of the spongy bone (1).

* * * * *